(12) United States Patent
Otto et al.

(10) Patent No.: US 11,166,781 B2
(45) Date of Patent: Nov. 9, 2021

(54) SYSTEM, METHOD AND SOFTWARE PROGRAM FOR AIDING IN POSITIONING OF A CAMERA RELATIVE TO OBJECTS IN A SURGICAL ENVIRONMENT

(71) Applicant: MAKO Surgical Corp., Ft. Lauderdale, FL (US)

(72) Inventors: Jason Karl Otto, Sioux Falls, SD (US); Matthew Thompson, Woodbridge, CT (US); Mark Ellsworth Nadzadi, Memphis, TN (US); Roberto Montane, Boca Raton, FL (US); Jonathan Morgan, Biscayne Park, FL (US); Bojan Gospavic, Boca Raton, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 0 days.

(21) Appl. No.: 16/390,730

(22) Filed: Apr. 22, 2019

(65) Prior Publication Data

US 2019/0321126 A1 Oct. 24, 2019

Related U.S. Application Data

(60) Provisional application No. 62/661,354, filed on Apr. 23, 2018.

(51) Int. Cl.
*G09G 5/00* (2006.01)
*A61B 90/00* (2016.01)
(Continued)

(52) U.S. Cl.
CPC ............ *A61B 90/361* (2016.02); *A61B 34/20* (2016.02); *A61B 90/37* (2016.02); *A61B 34/70* (2016.02); *A61B 2034/2057* (2016.02)

(58) Field of Classification Search
CPC ...... G06F 16/248; G06F 1/1647; G06F 3/048; G06F 30/00; H04N 21/4316;
(Continued)

(56) References Cited

U.S. PATENT DOCUMENTS 5,251,127 A 10/1993 Raab
6,187,018 B1 2/2001 Sanjay-Gopal et al.
(Continued)

FOREIGN PATENT DOCUMENTS

WO 2004069074 A1 8/2004
WO 2005076033 A1 8/2005
(Continued)

OTHER PUBLICATIONS

English language abstract and machine-assisted English translation for WO 2005/076033 extracted from espacenet.com database on Aug. 1, 2019, 6 pages.
(Continued)

*Primary Examiner* — Weiming He
(74) *Attorney, Agent, or Firm* — Howard & Howard Attorneys PLLC

(57) ABSTRACT

Systems, methods and software are provided for aiding in positioning of a camera relative to objects in a surgical environment. The camera has a 3D field of view and senses positions of the objects in the field of view. A controller is coupled to the camera and defines a first zone and a second zone within the field of view. Each zone defines a range of acceptable positions for one of the objects relative to a position of the camera. The controller receives the position of the objects. A graphical user interface displays image representations of: the field of view, the first zone relative to the field of view, the second zone relative to the field of view, the position of one object relative to the first zone, and the position of another object relative to the second zone.

27 Claims, 7 Drawing Sheets

(51) Int. Cl.
*A61B 34/20* (2016.01)
*A61B 34/00* (2016.01)

(58) Field of Classification Search
CPC ........... H04N 5/44591; A61M 16/0616; A61B 1/00045; A61B 34/20; A61B 34/25
See application file for complete search history.

(56) References Cited

U.S. PATENT DOCUMENTS

| | | | |
|---|---|---|---|
| 6,675,040 | B1 | 1/2004 | Cosman |
| 6,851,855 | B2 | 2/2005 | Mitschke et al. |
| 6,859,661 | B2 | 2/2005 | Tuke |
| 7,594,933 | B2 | 9/2009 | Kammerzell et al. |
| 7,660,623 | B2 | 2/2010 | Hunter et al. |
| 8,548,779 | B2 | 10/2013 | Ortmaier et al. |
| 8,890,511 | B2 | 11/2014 | Belew |
| 8,990,052 | B2 | 3/2015 | Lavallee et al. |
| 9,247,998 | B2 | 2/2016 | Hladio et al. |
| 9,248,001 | B2 | 2/2016 | Colombet et al. |
| 9,314,188 | B2 | 4/2016 | Hladio et al. |
| 9,408,557 | B2 | 8/2016 | Stein et al. |
| 9,480,534 | B2 | 11/2016 | Bowling et al. |
| 9,572,682 | B2 | 2/2017 | Aghazadeh |
| 9,684,768 | B2 | 6/2017 | Lavallee et al. |
| 2006/0241405 | A1 | 10/2006 | Leitner et al. |
| 2009/0012532 | A1 | 1/2009 | Quaid et al. |
| 2014/0276886 | A1 | 9/2014 | Stein et al. |
| 2015/0133945 | A1 | 5/2015 | Dushyant et al. |
| 2015/0185846 | A1* | 7/2015 | Otto ........................ G16H 50/50 345/156 |
| 2016/0106515 | A1 | 4/2016 | Kling et al. |
| 2016/0242858 | A1 | 8/2016 | Moctezuma de la Barrera et al. |
| 2016/0249968 | A1 | 9/2016 | Walter et al. |
| 2016/0256225 | A1 | 9/2016 | Crawford et al. |
| 2017/0172697 | A1 | 6/2017 | Aghazadeh |
| 2017/0224422 | A1 | 8/2017 | Bakirtzian et al. |
| 2017/0245946 | A1* | 8/2017 | Tabandeh ............... A61B 90/37 |
| 2018/0036884 | A1 | 2/2018 | Chen et al. |
| 2018/0064496 | A1 | 3/2018 | Hladio et al. |
| 2018/0168750 | A1 | 6/2018 | Staunton et al. |
| 2019/0054620 | A1 | 2/2019 | Griffiths et al. |
| 2019/0214126 | A1* | 7/2019 | Goetz ..................... G06T 19/00 |
| 2019/0290370 | A1 | 9/2019 | Brummund et al. |

FOREIGN PATENT DOCUMENTS

| | | |
|---|---|---|
| WO | WO 2005/076033 | 8/2005 |
| WO | 2013177334 A1 | 11/2013 |

OTHER PUBLICATIONS

International Search Report for Application No. PCT/US2019/028530 dated Jul. 26, 2019, 3 pages.
Mako Surgical Corp., "MAKOplasty Partial Knee Application User Guide", Rev., 03, Aug. 2013, 118 pages.
International Search Report for Application No. PCT/US2019/028530 dated ___ , ___ pages.

* cited by examiner

SYSTEM, METHOD AND SOFTWARE PROGRAM FOR AIDING IN POSITIONING OF A CAMERA RELATIVE TO OBJECTS IN A SURGICAL ENVIRONMENT

CROSS-REFERENCE TO RELATED APPLICATIONS

The subject application claims priority to and all the benefits of U.S. Provisional Patent App. Ser. No. 62/661,354, filed Apr. 23, 2018, the entire contents of which are hereby incorporated by reference in their entirety.

BACKGROUND

Modern surgical navigation typically involves at least some degree of preoperative planning of surgery and system setup in the operating room.

For surgical navigation systems, a camera is placed in the operation room and objects, such as trackers, are placed in the field of view of the camera. The camera optically tracks the positioning of the objects to provide tracking data that is utilized for purposes, such as guided control of the tool relative to the anatomy. For example, a robotic manipulator system may utilize the tracking data to guide the tool.

However, placing the camera at the optimal position and orientation relative to the objects in 3D space is no trivial task and conventionally requires much trial and error in repositioning the camera before proper setup. Even if the objects are within the camera field of view, the camera may still not be optimally placed in 3D space. For example, the camera may be placed too far/close or high/low relative to any one or more objects. Additionally, the horizontal positioning of the camera (too far left or too far right) has an impact on accuracy of camera placement. With several objects often used in the operating space, finding the camera placement to optimally satisfy this delicate balance has proven to be burdensome. In turn, the overall time required for preoperative setup is increased.

Moreover, any improper positioning of the camera may have detrimental consequences on the procedure. There may be instances where the camera placement, while preoperatively acceptable, becomes unacceptable during the procedure. In such instances, the procedure must be delayed until proper camera positioning can be obtained.

Furthermore, in some surgical procedures, parts of a patient should remain within the camera field of view throughout the surgical procedure to decrease the chances of misalignment, improper implant placement, and the like. For example, in an orthopedic procedure such as knee surgery, a ligament should maintain a constant length during flexion-extension movements. To achieve this purpose, the ligament must be positioned in such a way that the distance between points on the femur and tibia remain constant and optimally within the camera field of view.

As a result, there is a need in the art for proper positioning systems and methods designed to overcome at least the aforementioned technical problems.

SUMMARY

This Summary introduces a selection of concepts in a simplified form that are further described below in the Detailed Description below. This Summary is not intended to limit the scope of the claimed subject matter nor identify key features or essential features of the claimed subject matter.

One embodiment of a system is provided. The system comprises a camera having a three-dimensional field of view and being configured to sense a position of a first object and a position of a second object in the field of view. The system comprises a controller coupled to the camera and configured to define a first zone within the field of view at a first location and the first zone defining a range of acceptable positions for the first object relative to a position of the camera. The controller is configured to define a second zone within the field of view at a second location different from the first location and the second zone defining a range of acceptable positions for the second object relative to the position of the camera. The controller receives the position of the first object and the position of the second object. The controller executes a graphical user interface configured to aid in positioning of the camera relative to the first and second objects. The graphical user interface is configured to display image representations of the field of view, the first zone relative to the field of view, the second zone relative to the field of view, the position of the first object relative to the first zone, and the position of the second object relative to the second zone.

One embodiment of a method of operating a system is provided. The system comprises a camera having a three-dimensional field of view and being configured to sense a position of a first object and a position of a second object in the field of view, and a controller coupled to the camera. The method comprises defining, with the controller, a first zone within the field of view at a first location and the first zone defining a range of acceptable positions for the first object relative to a position of the camera. The method comprises defining, with the controller, a second zone within the field of view at a second location different from the first location and the second zone defining a range of acceptable positions for the second object relative to the position of the camera. The method comprises receiving, with the controller, the position of the first object and the position of the second object. The method comprises executing, with the controller, a graphical user interface to aid in positioning of the camera relative to the first and second objects and the graphical user interface displaying image representations of the field of view, the first zone relative to the field of view, the second zone relative to the field of view, the position of the first object relative to the first zone, and the position of the second object relative to the second zone.

One embodiment of a non-transitory computer readable medium is provided. The non-transitory computer readable medium comprises instructions, which executed by one or more processors, implement a graphical user interface to aid in positioning of a camera relative to a first object and a second object. The camera has a three-dimensional field of view and is configured to sense a position of a first object and a position of a second object in the field of view. A controller comprises the one or more processors and is coupled to the camera and configured to execute the graphical user interface. The graphical user interface displays image representations of the field of view of the camera, a first zone within the field of view at a first location and the first zone defining a range of acceptable positions for the first object relative to a position of the camera, a second zone within the field of view at a second location different from the first location and the second zone defining a range of acceptable positions for the second object relative to the position of the camera, the position of the first object relative to the first zone, and the position of the second object relative to the second zone.

DETAILED DESCRIPTION

Systems, methods, and software are disclosed for aiding in positioning of a localizer (e.g., camera) in an operating room relative to objects being sensed by the camera. The following description is focused on procedures for the knee or hip. The part to be treated is an anatomical part of a patient, and more specifically can be a bone, such as the pelvis, vertebra, femur, and/or tibia. However, the techniques described herein are not limited to these specific procedures. For example, the system may be used for camera placement assistance for neurosurgery, outpatient surgery, other orthopedic surgery, or for any other positioning of the camera relative to objects for any other application, surgical or non-surgical.

I. Overview of the System

Figure 1:
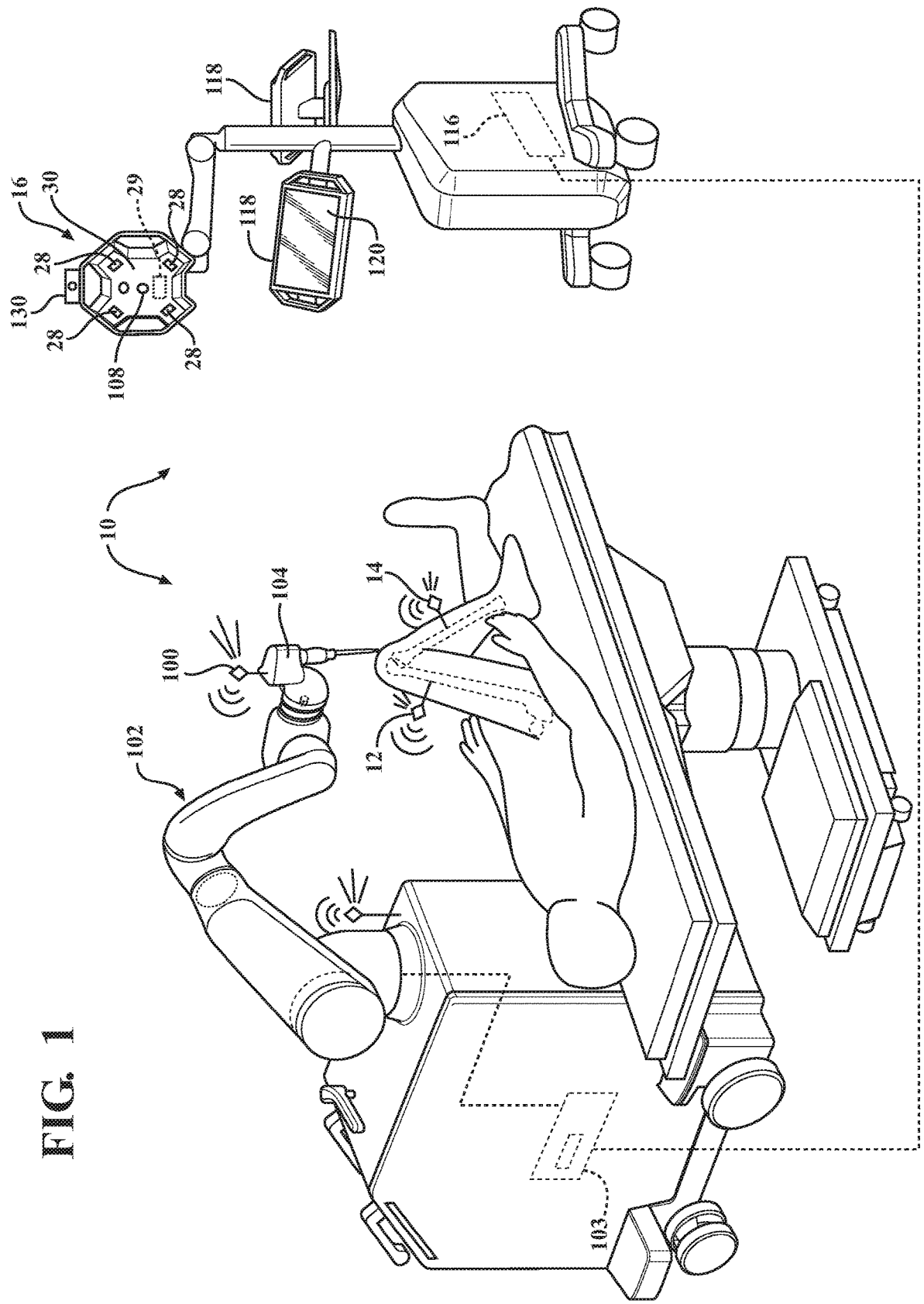
FIG. 1 is a perspective view of one example of a surgical system including a first object (e.g, tracker), a second object (e.g, tracker), a camera, and a controller for aiding in camera positioning.

Referring to FIG. 1, one example of a system 10 includes a first tracker 12, a second tracker 14, a camera 16, and various other components, which will be described below. The system 10 shown is in a surgical setting such as an operating room of a medical facility. As will be described in detail further below, the camera 16, having a three-dimensional field of view 20, is configured to sense a position 22 of a first object, such as first tracker 12 and a position 24 of a second object, such as a second tracker 14 for purposes of aiding in camera 16 positioning. In some cases, the purposes may include aiding in placement of trackers 12, 14 relative to a preferred zone or boundary within the field of view 20.

The systems and methods described herein may be applied to systems and methods comprising a plurality of trackers and/or cameras. Furthermore, the system and methods described herein may be utilized with or without trackers.

If trackers are utilized, the trackers are configured to couple to, attach to, or otherwise be integrated with the object being tracked. The camera 16 is able to track the respective object by tracking the position and/or orientation of the respective trackers. The techniques described herein may be utilized with any number of trackers.

Furthermore, as will be described below, the anatomy itself or any other object in the operating room may be the object that is detected by the system 10 (with or without trackers). In such instances, a machine vision system or laser range finder may be utilized to sense a position 22 of the first object and a position 24 of the second object for purposes of aiding in camera 16 positioning. In some cases, the purposes may include aiding in placement of objects relative to a preferred zone or boundary within the field of view 20. Hence, any of the techniques described below in reference to the trackers 12, 14, 100 may alternatively be utilized for any object sensed by the camera 16 which is not a tracker. Such objects may include, but are not limited to, tables, surgical instruments, anatomical parts, robotic manipulators, pointer devices, tool accessories, drapes, retractors, or any other component or subject of a surgical system for which the position of such object relative to the camera 16 may require guidance.

In the illustrated configuration of FIG. 1, for knee surgery, a first tracker 12 may be attached to the femur bone of the patient and a second tracker 14 may be attached to the tibia bone of the patient. Trackers 12, 14 may be firmly affixed to sections of the bone. In other configurations, the first and/or second trackers 12, 14 may be attached to a pelvic bone to track a position and orientation of the pelvic bone. In further configurations, the trackers 12, 14 may be mounted to other tissue types or parts of the anatomy, such as the spine.

In some configurations, a third tracker 100 may be attached to a robotic manipulator 102. The third tracker 100 may be attached to the robotic manipulator 102 in any suitable location. Moreover, any number of trackers may be fixed to any one object. For instance, the robotic manipulator 102 may comprise one tracker at a base of the manipulator and another tracker 100 at a surgical instrument 104 coupled to the robotic manipulator 102.

The third tracker 100, in this configuration, may be integrated into the surgical instrument 104 during manufacture or may be separately mounted to the surgical instrument 104 in preparation for the surgical procedure. Any number of surgical instruments 104 (whether coupled to the robotic manipulator 102 or not) may be tracked by attachment of a tracker including, but not limited to, a probe, scalpel, suction device, pin, clamp, or a hand-held robotic tool. The trackers 12, 14, 100 may be attached to one or more objects using any suitable method.

The trackers 12, 14, 100 may include one or more tracking elements or markers 26. The tracking markers 26 may be passive, active or combinations thereof. An example of an active marker may include, but not limited to, IR emitters, e.g. IR emitting LEDs, or the like. In one configuration, at least three active tracking markers 26 are used for a tracker 12, 14, 100. In some configurations, active tracking markers 26 may be sequentially fired, for transmitting light signals to the optical sensors or other tracking sensors 28 of the camera 16. An example of a passive marker 26 may include, but not limited to, reflectors that reflect light emitted from the tracking sensors 28 or the like. The reflected light may be received by the tracking sensors 28 for tracking purposes. Any number of tracking markers 26 may be utilized for any given tracker 12, 14, 100.

Figure 3:
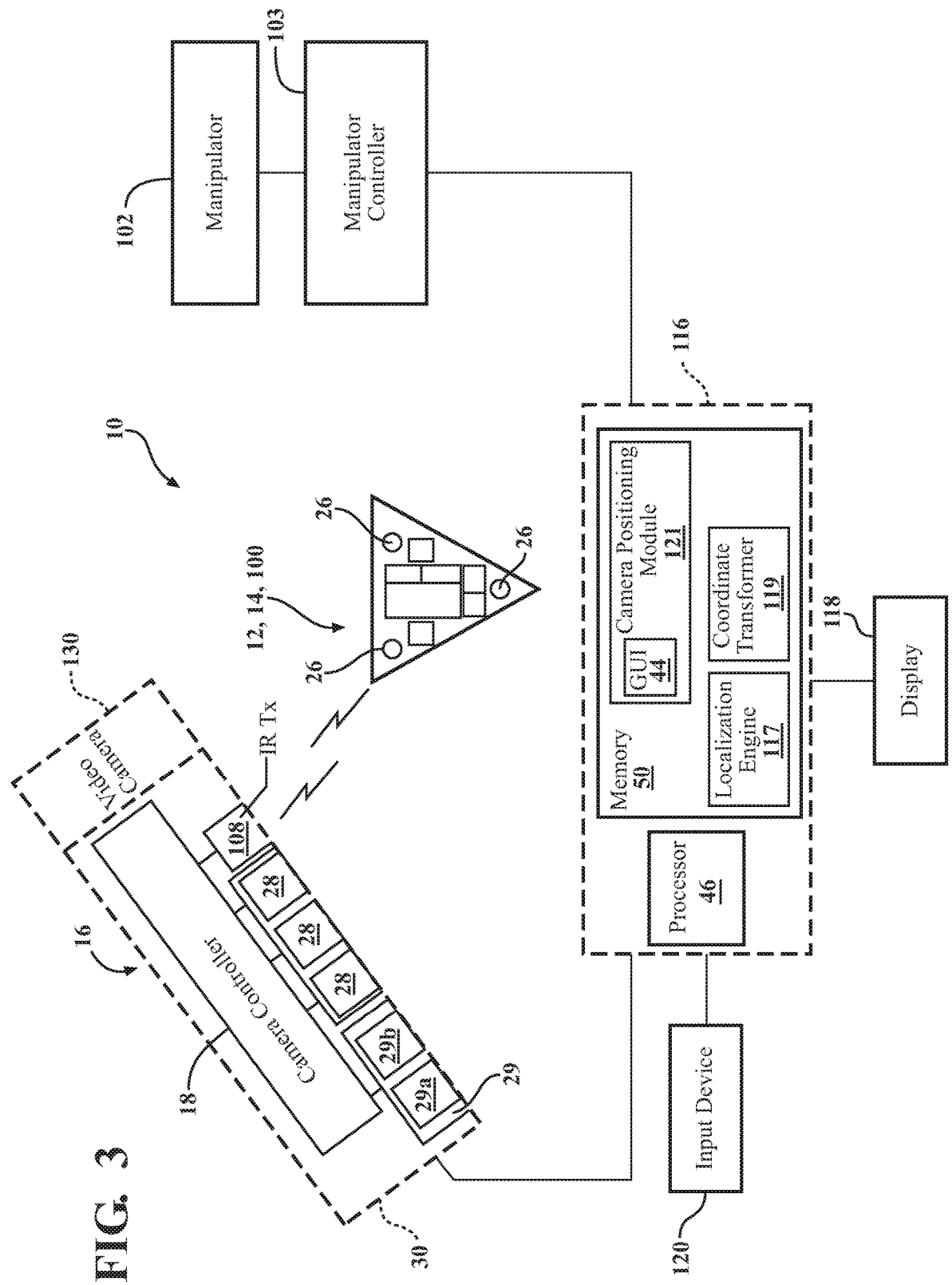
FIG. 3 is a block diagram of the surgical system according to one example.

As shown in FIG. 3, the system 10 may comprise one or more controllers or computing devices. In the example, shown, the system 10 includes a camera controller 18, a manipulator controller 103, and a navigation computer 116. Any of the controllers 18, 103, 116 may comprise any suitable number and types of microcontrollers, processors, integrated circuits, memory and software modules comprising instructions that can be executed for performing the respective capabilities described herein. The controllers 18, 103, 116 can be separate devices or combined into a single device. The controllers 18, 103, 116 can be located in the respective devices shown in FIG. 3, or can be located in other devices. The capabilities of the controllers 18, 103, 116 will be described further below.

Any of the trackers 12, 14, 100 may be battery powered with an internal battery or may be leads to receive power through the controller 18, which like the camera 16, preferably receives external power. In other words, any of the trackers 12, 14, 100 can be self-powered with an internal power supply or may receive power through a host object, if available. Trackers 100 other than trackers 12, 14 specifically shown in the figures are fully contemplated. Such other trackers 100 may be provided for purposes of tracking any object other than those shown in FIG. 1.

The camera 16 is implemented to cooperate with the trackers 12, 14 to determine a position 22, 24 for each tracker 12, 14. In one embodiment, the camera 16 operates by line-of-sight, meaning that tracker 12, 14 position 22, 24 may be obstructed to the camera 16 by presence of an intermediate object therebetween.

The camera 16 may be employ different modalities and may alternatively be an electromagnetic-based, RF-based, ultrasound-based, or any other types of localization device capable of tracking and/or sensing one or more objects/trackers. In some instances, the localization device may include additional sensing and/or tracking devices.

Additionally, the camera 16 is configured to determine a pose (i.e. a position and orientation) of one or more objects and/or trackers before and during a surgical procedure to detect movement of the object(s). For example, before a surgical procedure, objects may be moved around the operating room in preparation. The camera 16 may include a detection device that obtains a pose of an object with respect to a coordinate system of the detection device. As the object moves in the coordinate system, the detection device tracks the pose of the object. As a result, control parameters may be adjusted by the controller 18 in response to movement of objects in the operating room. Based on the control parameters, the user and/or the controller 18 may be guided to optimally position the camera 16 before the surgical procedure.

Figure 2:
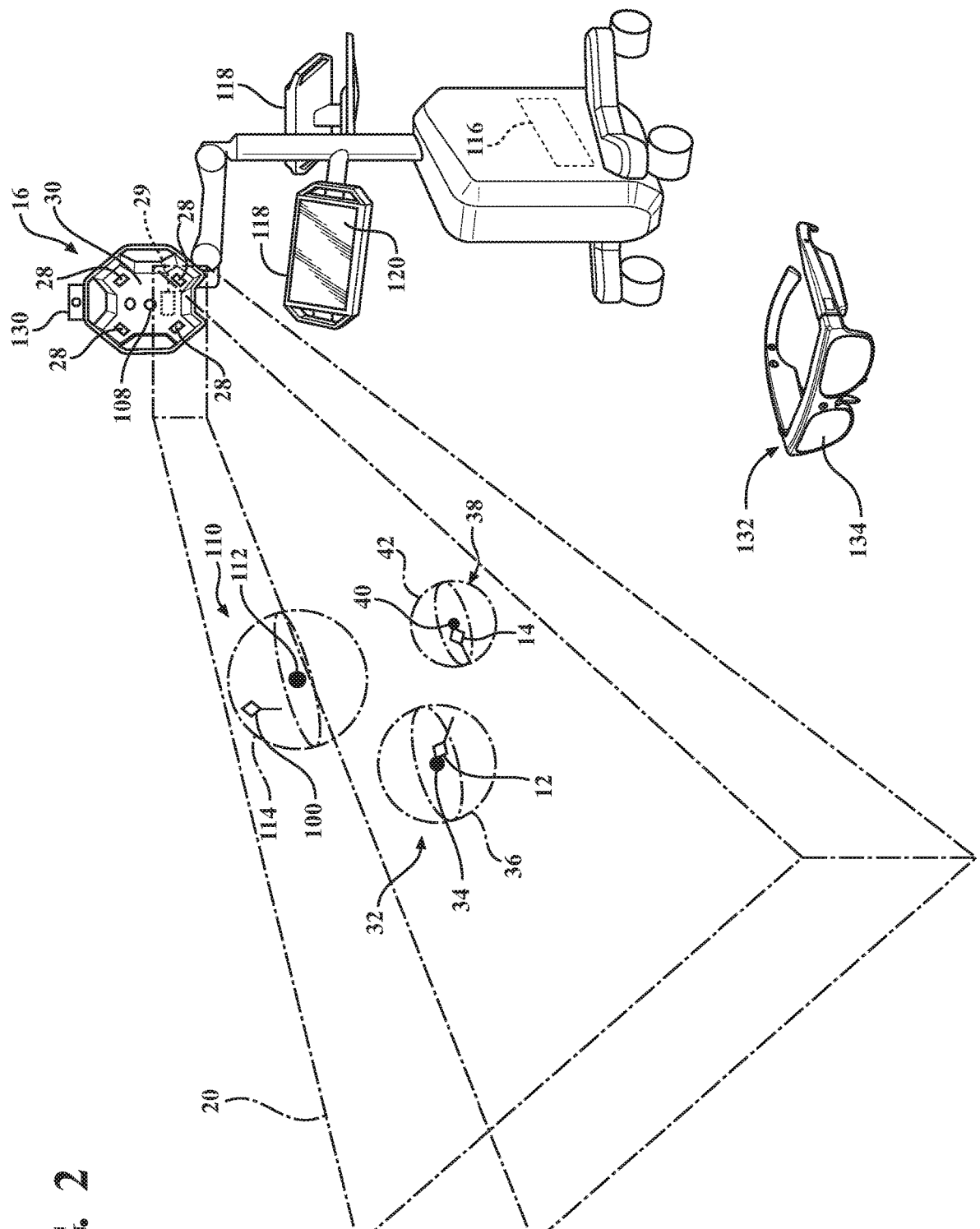
FIG. 2 is a perspective view of one example of a three-dimensional field of view of the camera, a first zone within the field of view at a first location with the first zone defining a range of acceptable positions for the first object, a second zone within the field of view at a second location with the second zone defining a range of acceptable positions for the second object, and a third zone within the field of view at a third location with the third zone defining a range of acceptable positions for a third object.

In some configurations, the system 10 may comprise a video camera 130, as shown for example, in FIGS. 2 and 3. The video camera 130 can be attached to the camera unit 30 or spaced apart and at a different location from the camera unit 30. The video camera 130 can be orientated such that the field of view 20 of the camera 16 may be associated with the field of view of the video camera 130. In other words, the two fields of view may be matched or otherwise correlated such that if an object can be seen in video images streamed from the video camera 130, the object(s) are also within the field of view 20 of the camera 16. Any suitable calibration procedure may be utilized to associate a coordinate system of the video camera 130 with the coordinate system of the camera 16, such as imaging of a calibration unit, image or light pattern. Video images can be streamed to displays before and/or during surgical procedures.

The video camera 130 described above may be integrated into a machine vision system of the system 10 with ability to identify the anatomy of the patient and/or any other object in the operating room using machine vision technology. Once the anatomy of the patient or any other object in the operating room is identified and shown on displays, the controller 18 may determine optimal positioning for the camera 16 and/or the objects, while simultaneously and continuously showing the video images from the video camera 130 or machine vision camera, which shows the user and/or the controller 18 positioning the camera 16 and/or the objects.

The machine vision system utilizing the camera 16 and/or the machine vision camera is able to detect movement of these objects by continuously taking images, reviewing the images, and detecting movement of the objects. In some cases, position information from the machine vision system for the objects may be transmitted to the controller 18. Likewise, position information from the controller 18 and/or the camera 16 may be transmitted to the machine vision system. The machine vision system could be used to aid the user and/or the controller 18 in positioning of the camera 16 and/or the trackers 12, 14 by defining the pose of one or more objects in the operating room.

Machine vision may be used for camera placement even when objects are not moved, but are stationary. In this case, trackers may not be required for position measurement and machine vision need not detect the anatomy. Instead, machine vision could provide distance information for any objects detected in the operating room, including trackers. The distance information can be the distance between the machine vision camera and the respective object. The distance information can be presented by the GUI 44 on any suitable display. The distance information could be associated with or displayed by or on actual or virtual image representations of the surgical site or any objects therein detected by the machine vision camera. With this technique, the user can visually see the distances presented on the GUI 44 to aid the user in placing the camera 16.

The machine vision system may utilize any suitable image processing algorithm for determining such distance information, including, but not limited to utilizing a depth map generation, segmentation, edge detection, color analysis, blob detection, pixel analysis, pattern recognition, or the like. These algorithms can be executed by any one or more of the controllers described herein.

According to one example, as mentioned above, the camera 16 may include a plurality of tracking sensors 28 for tracking the respective positions 22, 24 of the trackers 12, 14. In one example, the tracking sensors 28 are integrated on the camera unit 30. The camera unit 30 includes any number of tracking sensors 28. The tracking sensors 28 are configured to detect the position 22, 24 of the tracking markers 26 of the respective trackers 12, 14. The tracking sensors 28 may be positioned in areas other than on the camera unit 30. The tracking sensors 28 are configured to receive IR signals and data from the trackers 12, 14 over an IR spectrum.

In one configuration, the tracking sensors 28 are optical sensors, and more specifically, IR sensors. Each of the tracking sensors 28 is configured to detect IR signals through the IR spectrum. The camera 16 may comprise configurations or devices for detecting IR signals for tracking purposes using devices other than optical sensors or charged-coupled devices (CCD).

The camera 16 may comprise one or more IR transmitters 108 (IR Tx) for transmitting signals or data using IR communication for commanding and controlling the trackers 12, 14. The IR transmitter 108 may be housed by the camera 16 unit or may be located elsewhere. The IR transmitter 108 is configured to wirelessly transmit IR signals to an IR receiver of the trackers 12, 14. The IR transmitter 108 may comprise one or more IR emitters, such as IR emitting LEDs, or the like.

The camera 16 is coupled to the controller 18. In one configuration, the camera 16 is coupled to the controller 18 via a direct connection. In another configuration, the camera 16 may be wirelessly coupled to the controller 18. The components of the system 10 can be interconnected by any form or medium of digital data communication (e.g. a communication network). Examples of communication networks include, but not limited to, a local area network (LAN), a wide area network (WAN), the internet, wired networks, and/or wireless networks.

The camera 16 may be adjustable in at least one degree of freedom and, in some configurations, in two or more degrees of freedom. The camera 16 may be mounted on an adjustable arm to position the tracking sensors 28 above an area in which the procedure is to take place to provide the camera 16 with a field of view 20 that is ideally free from obstruction. The adjustable arm may be position controlled by motorized joints. Alternatively, the adjustable arm may be manually controlled by a user.

As shown in FIG. 2, the three-dimensional field of view 20 comprises a trapezoidal configuration. The field of view 20 may be adjustable to any suitable shape or volume such that the field of view 20 encompasses any desired objects. Objects may include, but are not limited to, tables, surgical instruments, an anatomy, robotic manipulators, drapes, or any other component or subject of a surgical system.

Techniques for utilizing a camera for tracking the position of trackers can be like those described in U.S. patent application Ser. No. 13/958,834, entitled, "Navigation System for use with a Surgical Manipulator Operable in Manual or Semi-Autonomous Mode", the disclosure of which is hereby incorporated by reference.

Examples of trackers can be like those described in U.S. patent application Ser. No. 15/840,278, filed on Dec. 13, 2017, entitled "Techniques for Modifying Tool Operation in a Surgical Robotic System Based on Comparing Actual and Commanded States of the Tool Relative to a Surgical Site," the entire disclosure of which is hereby incorporated by reference in its entirety.

Software or firmware to implement the techniques and/or methods introduced herein may be stored on a non-transitory computer readable medium or memory 50 comprising instructions. The memory 50 may be stored on a computer 116 that runs the software for the camera 16, or navigation system generally.

As shown in FIG. 3, the system 10 may comprise one or more processors 46 to execute software modules/programs such as a localization engine 117 and a coordinate transformer 119. These software modules/programs collaborate to process the signals transmitted according to any communication methods, for example IR and RF, to transform coordinate systems of the trackers, and consequently the object being tracked, into a coordinate system of the camera 16 for purposes as determining relative position of the camera 16 to the surgical site (e.g. the bone of the patient). This data may be forwarded to a manipulator controller 103 from the controller 18 to control the manipulator 102 and corresponding movement of the surgical instrument 104.

The computer 116 may be coupled to a display device 118 and an input device 120 (e.g., a touch screen, keyboard, mouse, gesture control, voice control, etc.).

The computer 116, in communication with the camera 16, the controller 18, and the manipulator controller 103, may simulate a surgical procedure during pre-operative planning. Pre-operative planning and/or simulation may be specific to the type of surgery and/or patient. Based on the pre-operative simulation, the controllers 18, 103 may determine optimal positioning of objects including, but not limited to, the camera, surgical table, lights, displays, trackers, patient, and robotic manipulator.

Alternatively or additionally, pre-defined data such as surgeon height, patient height, table height, and the like may be stored in memory 50 for use during pre-operative simulation. Such pre-defined data may exist in memory 50 for any particular surgeon, patient, or given type of procedure and may be loaded from memory 50 depending on the surgeon, the patient and the type of procedure selected for the system 10. Thus, the pre-defined data may aid in determining optimal positioning of objects in an operating room. In another configuration, the user may use the input device 120 to input the pre-defined data before a surgical procedure for use during pre-operative simulation and/or during a surgical procedure. In another configuration, the pre-defined data may be inferred by the controller 18 and/or the machine vision system.

During the pre-operative planning, the controllers 18, 103 may determine a range of motion of the robotic manipulator 102 and/or the patient to aid in positioning of the camera 16 and/or the trackers 12, 14, 100. Knowing the ranges of motion of the robotic manipulator 102 and/or the patient, a preferred or ideal position for each tracker 12, 14, and 100 may be defined prior to the surgical procedure or as each tracker is placed. For example, once the first tracker 12 is placed, the position of the first tracker 12 dictates the preferred position of the second tracker 14, and so on. In another example, the tracker 100 may be placed before the placement of the trackers 12, 14, and thereafter, the controllers 18, 103 may determine the preferred position of the robotic manipulator 102 relative to the patient. Additionally, once the trackers 12, 14 are placed, the controllers 18, 103 may indicate repositioning of the robotic manipulator 102 is required.

On the other hand, during the pre-operative planning, the range of motion of the robotic manipulator 102 and/or the patient may be determined after the placement of the trackers 12, 14, 100. Further, the range of motion of the robotic manipulator 102 and the patient may be re-defined after the placement of the trackers 12, 14, 100.

Additionally, knowing the range of motion of the robotic manipulator 102 and the patient, the acceptable positioning of the camera 16 and/or the field of view 20 may be adjusted to optimally sense and/or track the trackers 12, 14.

II. Techniques for Aiding in Camera Placement

As shown in FIG. 3, the computer 116 may further comprise a camera positioning module/program 121 configured for aiding in positioning of a camera 16 relative to the objects in the operating room, such as, but not limited to, the first and second trackers 12, 14. Although systems and methods described herein may be applied to systems including one or more trackers, the description below refers generally to the first tracker 12 and the second tracker 14 for simplicity in description.

When executed by one or more processors 46, the instructions of the camera positioning module/program 121 are configured to implement a graphical user interface (GUI) 44.

The GUI 44 is displayed on the display 118 and the user can interact with the GUI 44 with the input device 120.

Figure 4:
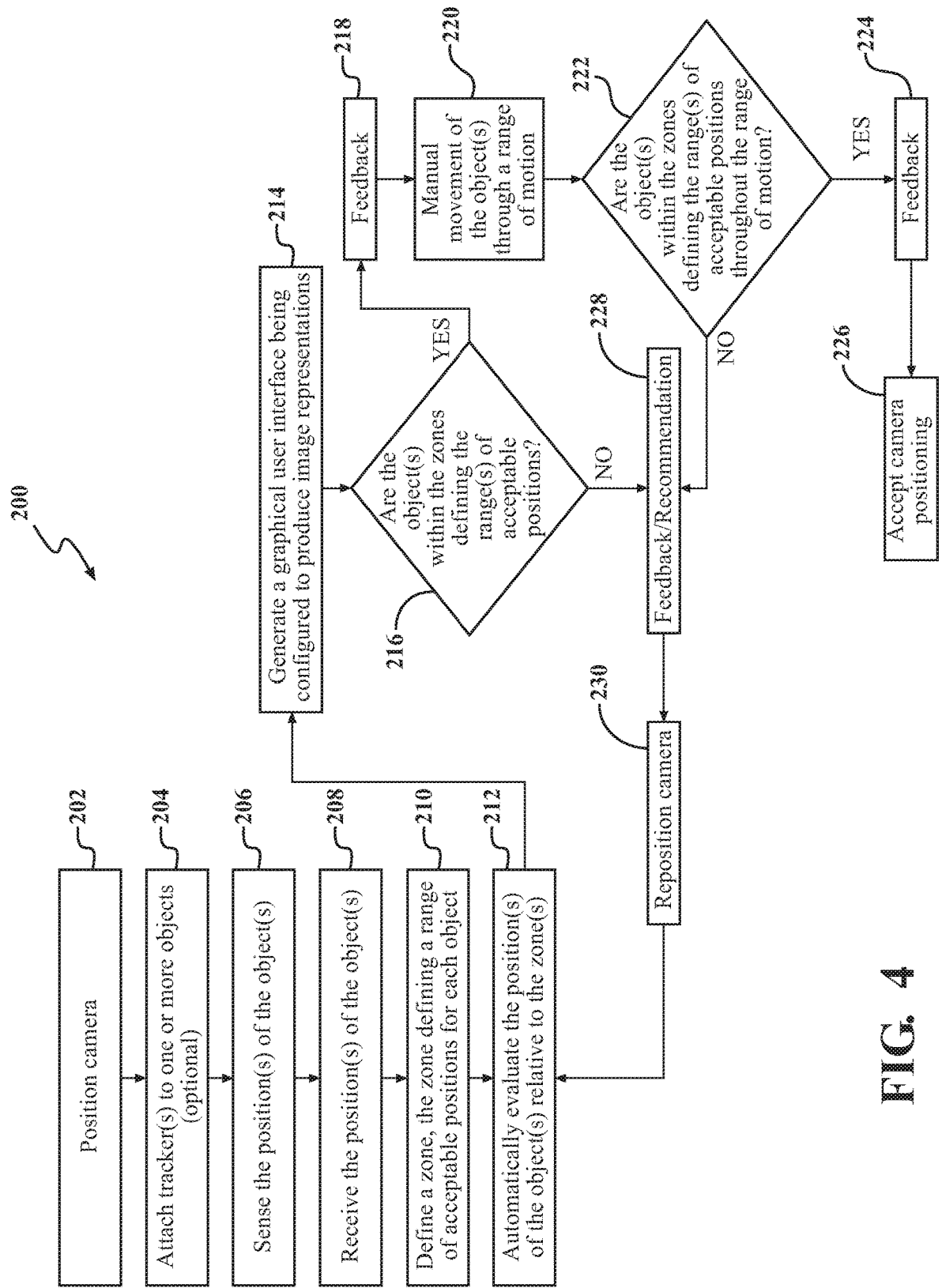
FIG. 4 is a block diagram of a method for positioning a camera relative to the objects, according to one example.

FIG. 4 shows a method 200 for aiding in positioning of a camera 16 relative to the first and second trackers 12, 14 using the camera positioning module/program 121.

The steps of the method 200 may be carried out in the order shown. Other orders of these steps are also contemplated. Furthermore, some of the following steps may be combined into one step, or may be optional to the method 200. The method 200 starts at step 202 wherein the camera 16 is positioned. The camera 16 may be manually positioned by the user or positioned by a semi-autonomous or fully-autonomous positioning system. If trackers 12, 14 are utilized, the next step is 204 wherein the trackers 12, 14 are optionally attached to one or more objects. When using the machine vision system and/or laser range finder, the trackers 12, 14 may or may not be attached to the objects. In one method 200*a*, step 202 and step 204 may be implemented at the same time. In another method 200*b*, step 202 may be implemented before step 204. It will be appreciated that steps 202-204 may not be required as part of the method 200.

At step 206, the position 22, 24 of the objects is sensed within the field of view 20. The positions 22, 24 may be sensed by the camera 16 if the trackers 12, 14 are the objects being detected. More specifically, the camera 16 is configured to sense the position 22 of the first tracker 12 and the position 24 of the second tracker 14 in the field of view 20. Once the camera 16 senses the position 22, 24 of each tracker 12, 14, the camera 16 may be configured to transmit data regarding the positions 22, 24 to the controller 18. Alternatively, the machine vision system or the laser range finder may be utilized to sense the position of the objects within the field of view 20. In such instances, the trackers 12, 14 need not be utilized.

At step 208, the controller 18 receives the position 22 of the first object or tracker 12 and the position 24 of the second object or tracker 14. The transmission of the positions to the controller 18 may in incorporated at either step 206 or step 208. Such transmissions may be from the camera 16, the machine vision system, or the laser range finder.

At step 210, the controller 18 may be configured to define a first zone 32 within the field of view 20 at a first location 34 with the first zone 32 defining a (first) range 36 of acceptable positions for the first object or tracker 12 relative to the position of the camera 16. Furthermore, the controller 18 may also be configured to define a second zone 38 with the field of view 20 at a second location 40 with the second zone 38 defining a (second) range 42 of acceptable positions for the second object or tracker 14 relative to the position of the camera 16. Step 208 and step 210 may occur simultaneously or step 210 may occur before step 208.

In the configuration mentioned above, as shown in FIG. 2, the first range 36 and the second range 42 are each defined as a three-dimensional range of acceptable positions (e.g., a sphere). As shown throughout the Figures, the first zone 32 and second zone 38 are spherical in shape. The zones 32, 38 may be any suitable three-dimensional shape/volume. Other examples of 3D ranges include cones, cubes, hemi-spheres, or the like.

In some instances, the first range 36 and/or the second range 42 may be defined as a two-dimensional range of acceptable positions. For example, the ranges may be represented as 2D planes of any suitable shape (rectangular, circular, etc.).

The first zone 32 may be configured to be a different shape from the second zone 38. For example, the first zone 32 may be configured to be spherical in shape and the second zone 38 may be configured to be cubic in shape. It will understood that the first range 36 of acceptable positions and the second range 42 of acceptable positions may comprise the shape of the first zone 32 and the second zone 38, respectively.

The controller 18 may be configured to define any number of zones within the field of view 20 associated with any number of objects or trackers. For example, the controller 18 may be configured to define a third zone 110 within the field of view 20 at a third location 112 associated with the third object or tracker 100 wherein the third zone 110 defines a (third) range 114 of acceptable positions for the third object or tracker 100 relative to the position of the camera 16.

Different locations 34, 40, 112 of the zones 32, 38, 110 means that the zones 32, 38, 110 (as defined by their acceptable ranges 36, 42, 114) are originated at different Cartesian coordinates in 2D or 3D space, as shown in FIG. 2. Although the acceptable ranges 36, 42, 114 may overlap in certain instances, the median/center of the range (for 2D) or the volumetric center point (for 3D) of the ranges are located at different positions.

The acceptable ranges 36, 42, 114 may be defined by the camera positioning module 121, by a user, or by the specific procedure. As used herein, the term "acceptable position" is defined as a preferred or optimal position of the object or tracker 12, 14 relative to the camera 16, as either judged by the user and/or by any suitable processor, controller 18, and the like.

The acceptable ranges 36, 42, 114 may be predefined before the set-up of the camera 16 in the operating room. For example, from a pre-operative simulation, calibration data or optimal performance characteristics for the camera 16/tracker 12, 14 may be stored in memory 50 for defining the ranges 36, 42, 114. Such pre-defined data may exist in memory 50 for any given type of procedure (e.g., partial knee arthroplasty) and may be loaded from memory 50 depending on the type of procedure selected for the system 10. Thus, in one example, for step 210, the first zone 32 and the second zone 38 may be predefined before the set-up of the objects or trackers 12, 14.

Alternatively, the acceptable ranges 36, 42, 114 may be dynamically defined during the set-up of the camera 16 in the operating room. For example, the controller 18 may generate the ranges 36, 42, 114 on-the-fly depending upon an initial evaluation of the tracked positions of the objects or trackers 12, 14 relative to the camera 16, an evaluation of the current tracked positions relative to expected positions of the objects or trackers 12, 14, or the like. Thus, in another example for step 210, the first zone 32 and the second zone 38 may be dynamically defined during the set-up of the objects or trackers 12, 14. In other examples, the first zone 32 and/or the second zone 38 may be defined at the discretion of a user, a controller 18, and the like.

At step 212, wherein the controller 18 may be configured to automatically evaluate the position 22 of the first object or tracker 12 relative to the first zone 32 and the position 24 of the second object or tracker 14 relative to the second zone 38 based on the transmitted data from the camera 16. Additionally or alternatively, the user may visually evaluate the position 22 of the first object or tracker 12 relative to the first zone 32 and the position 24 of the second object or tracker 14 relative to the second zone 38.

Figure 5:
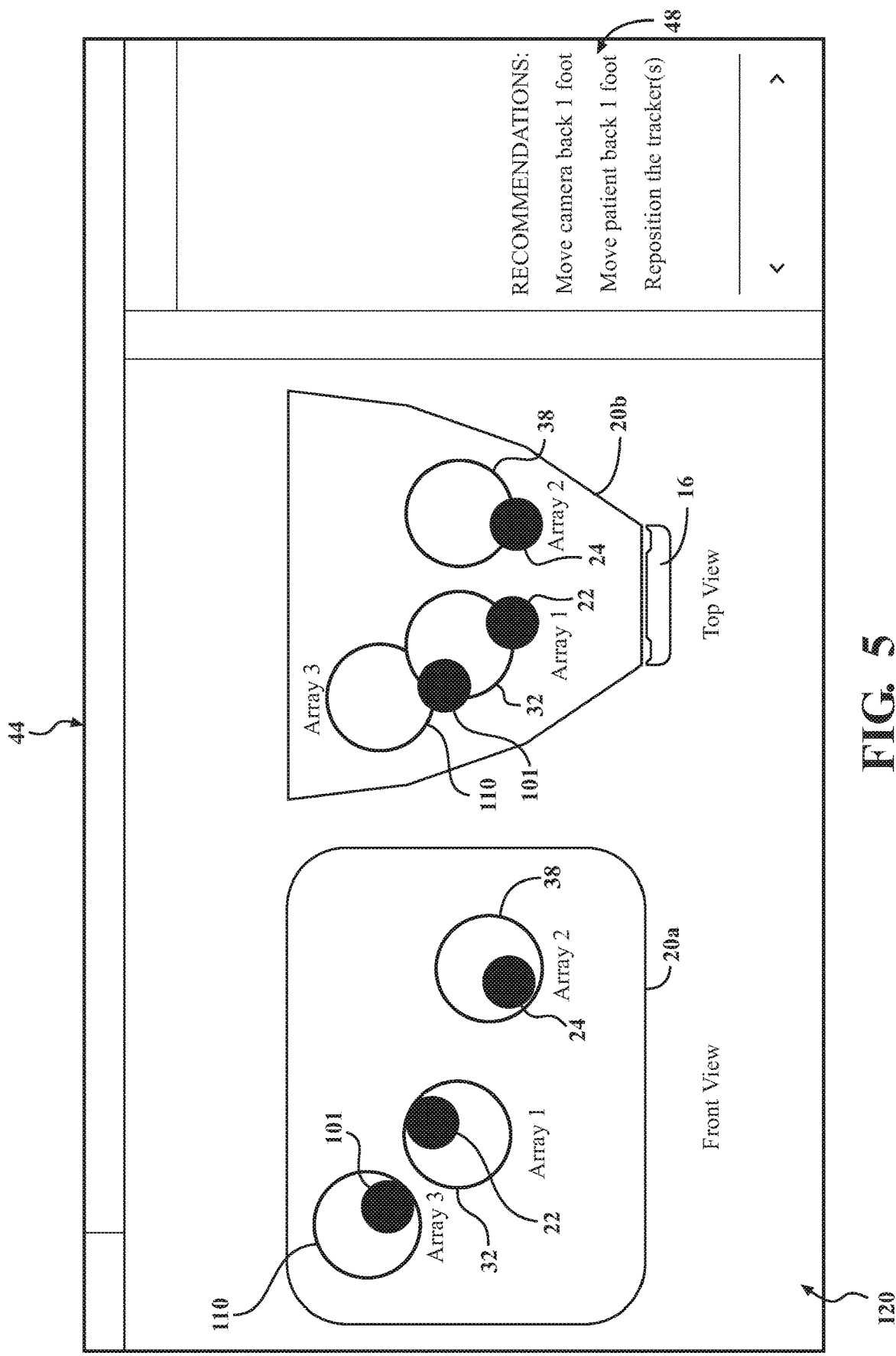
FIG. 5 is an illustration of one example of a graphical user interface being configured to produce image representations of the field of view with a first view and a second view, with each view showing the zones for the first, second and third objects, and further showing the tracked position of each object relative to each zone for each view.
Figure 6A:
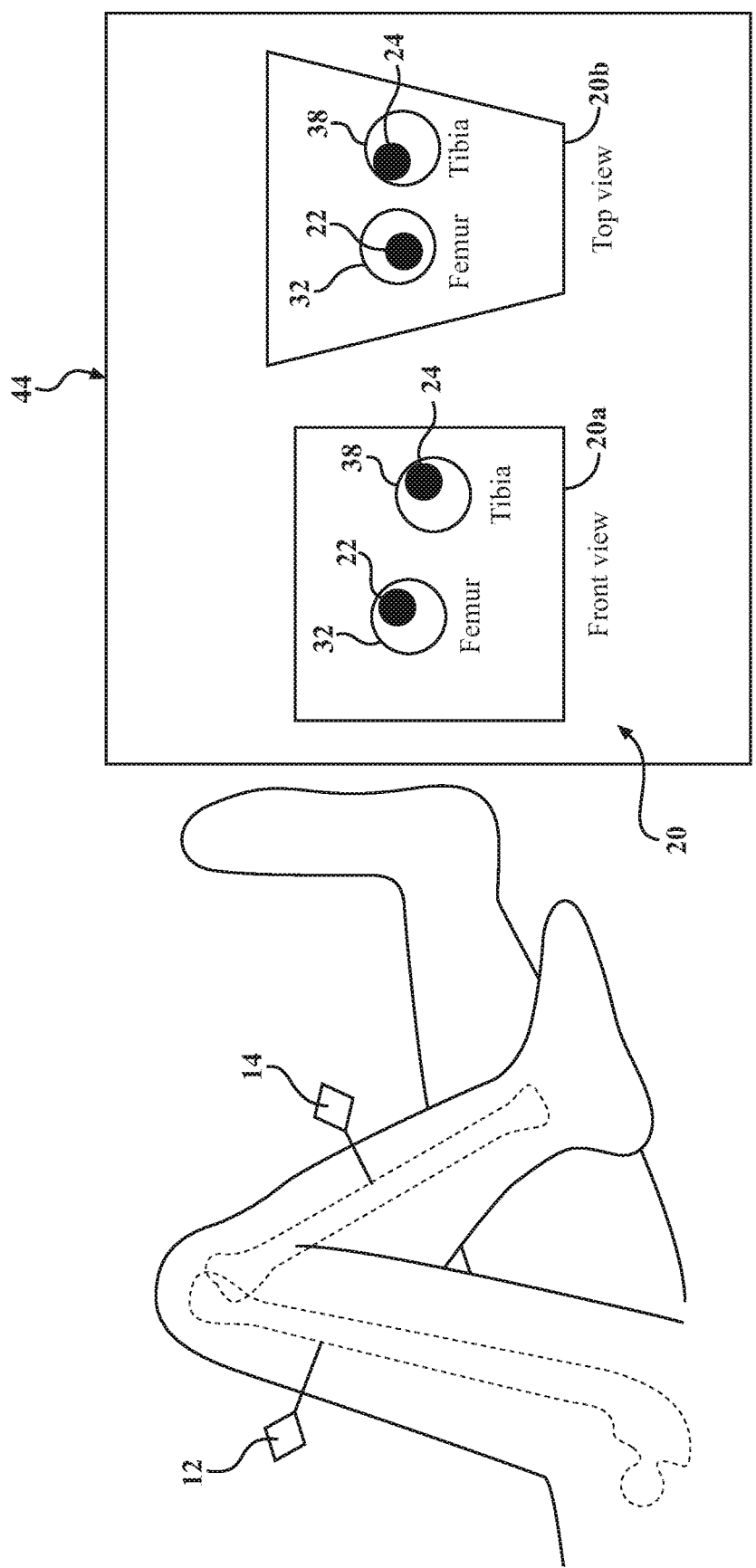
FIG. 6A is a perspective view of one example of the first object being attachable to a femur bone and a second object being attachable to a tibia bone with the patient's leg in a flexion position and showing a portion of the graphical user interface producing image representations the tracked positions of the objects relative to their respective zone for front and top views.
Figure 6B:
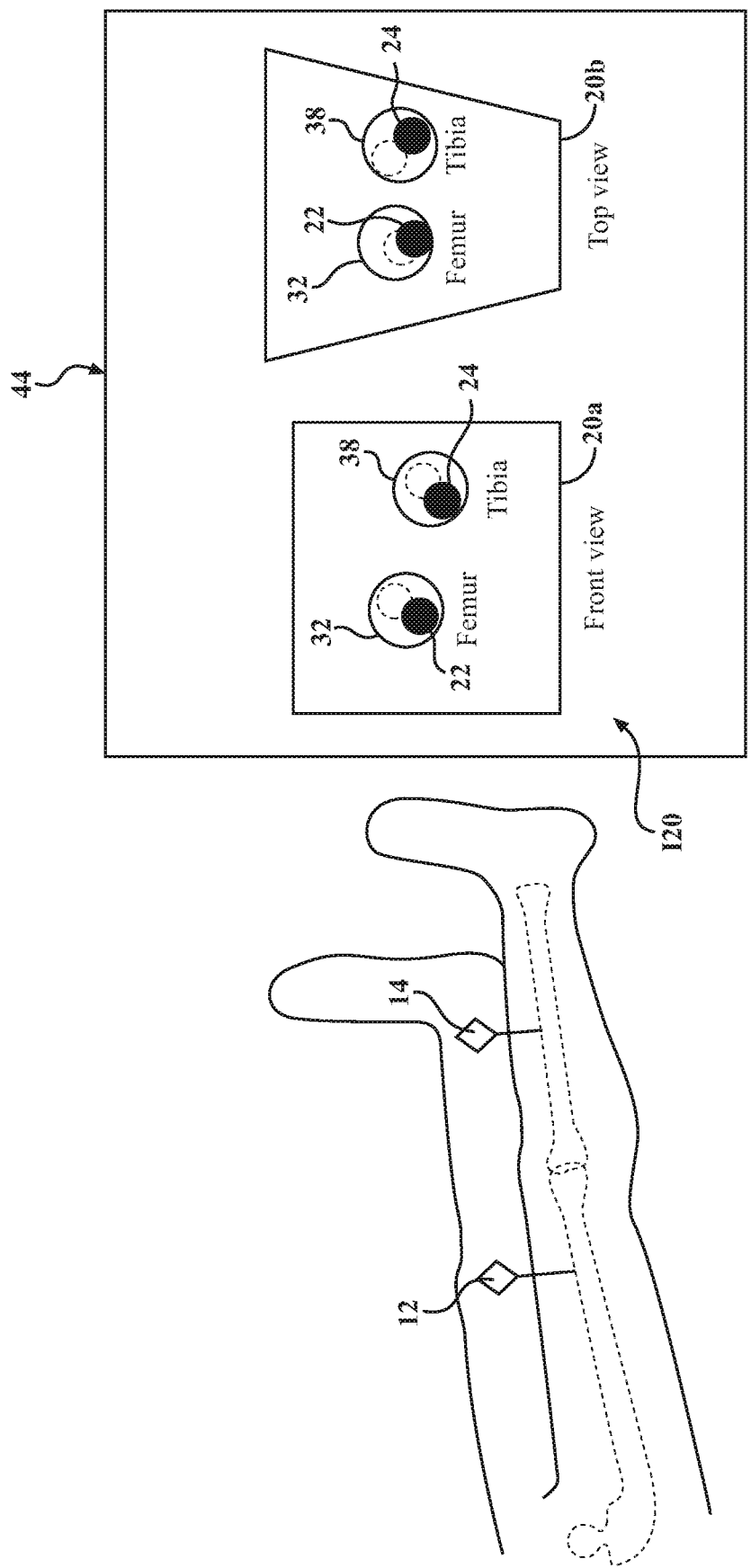
FIG. 6B is a perspective view of FIG. 6A with the patient's leg in an extension position and simultaneously showing the portion of the graphical user interface showing updated representations the tracked positions of the objects relative to their respective zone for front and top views as a result of leg extension.

At step 214, and as shown in FIGS. 5-6B, the controller 18 generates the GUI 44 configured to aid in positioning of the camera 16 relative to the first and second objects or trackers 12, 14. Guidance from the GUI 44 enables the user to actively, accurately, and visually determine if the camera 16 and/or the objects or trackers 12, 14 are acceptably positioned. This GUI 44 can be generated or adapted in the operating room. Alternatively or additionally, the GUI 44 can be preconfigured before the camera is utilized in the operating room.

The GUI 44 is configured to produce image representations to help achieve this goal. As used herein, "image representation" means that the GUI 44 graphically displays a static or dynamic object (e.g., image(s)) that is representative of the source object (e.g., tracker, field of view, zones, etc.). The displayed object provides the user with contextual meaning about the source so that the user can readily understand the significance of the object during camera setup. The displayed object on the GUI 44 may be a scaled version of the source object (or part of the object). The displayed object on the GUI 44 may be associated with the position of the object in space, etc.

More specifically, the GUI 44 produces image representations of the field of view 20, the first zone 32 relative to the field of view 20, the second zone 38 relative to the field of view 20, the position 22 of the first object or tracker 12 relative to the first zone 32, and the position 24 of the second object or tracker 14 relative to the second zone 38. In one configuration, the GUI 44 may be configured to produce image representations of the third zone 110 relative to the field of view 20 and the position 101 of the third object or tracker 100 relative to the third zone 110.

The GUI 44 may produce 2D, 3D, or a mixture of 2D/3D image representations of any of the aforementioned field of view 20, zones 32, 38, 110, objects or trackers 12, 14, 100. Any of the image representations can be real images, e.g., as taken in real time by the video camera 130. Additionally or alternatively, any of the image representations can be virtual images, e.g., simulations or computer models of the actual field of view 20, zones 32, 38, 110, objects or trackers 12, 14, 100. Combinations of real and virtual images can be utilized. In one example, the GUI 44 employs augmented reality to aid in positioning of the camera 16 relative to the objects or trackers 12, 14, 100. For example, the field of view 20 and/or zones 32, 38, 110 can be represented by virtual models (e.g., geometrical outlines) mixed with a real time image of the surgical field and objects or trackers 12, 14, 100 as captured by the video camera 130. In such examples, the position of the virtual model of the field of view 20 and/or zones 32, 38, 110 changes in real time relative to the actual images of objects or trackers 12, 14, 100 as the user moves the position of the camera 16. The GUI 44 and corresponding image representations can be shown on the display(s) 118 or on a digital transparent lens 134 of a head-mounted device 132 worn by the user setting up the camera 16.

The GUI 44 may be configured to further provide any visual data for surgical navigation purposes, such as schematic anatomic representations, images of diagnostic datasets, instructions or guides for surgical procedure, depiction of virtual and haptic objects, system status information, patient information, and other information that may be communicated to the user.

The GUI 44 may be configured to produce additional image representations including, but not limited to, objects in the operating room other than those described herein (e.g., objects to be avoided).

In one example, the GUI 44 can produce image representations of the field of view 20 from a first view 20*a* and a second view 20*b*. As shown in FIG. 5, the first view 20*a* is a front or point-of view and the second view 20*b* is a top view of the three-dimensional field of view 20. The two views 20*a*, 20*b* are two-dimensional representations of the three-dimensional shape of the field of view 20. In one configuration, the first view 20*a* is a bottom view and the second view 20*b* is a side view of the three-dimensional field of view 20. It will be appreciated that the two views 20*a*, 20*b* may be any combination of the top, bottom, front, back, right, left and the like view of the three-dimensional field of view 20 relative to the camera 16. The GUI 44 may provide any number of views (20*a*, 20*b*, 20*c*, and so on) of the three-dimensional field of view 20.

As shown in FIG. 5, the front view 20*a* is rectangular and the top view 20*b* is trapezoidal. However, the views 20*a*, 20*b* may be any suitable geometry. For example, if the three-dimensional field of view 20 is a prism in shape, the front view 20*a* may be triangular and the top view 20*b* may be rectangular. The views 20*a*, 20*b* may be perspectives of the field of view 20 from the first-person perspective of the camera 16. In other examples, the views 20*a*, 20*b* may represent the field of view 20 using shapes that are something other than a 2-D representation of the field of view 20 from different perspectives. For example, the views 20*a*, 20*b* may arbitrarily be chosen to be square shape.

With the two views 20*a*, 20*b*, as shown in FIG. 5, the GUI 44 may be configured to produce image representations of the first zone 32 relative to the field of view 20 from the first view 20*a* and from the second view 20*b* and the second zone 38 relative to the field of view 20 from the first view 20*a* and from the second view 20*b*. This graphical technique provides the user with an understanding of where the zones are relative to the field of view 20.

The GUI 44 further represents the position 22 of the first object or tracker 12 relative to the first zone 32 from the first view 20*a* and the position 22 of the first object or tracker 12 relative to the first zone 32 from the second view 20*b*. Similarly, the GUI 44 represents the position 24 of the second object or tracker 14 relative to the second zone 38 from the first view 20*a* and the position 24 of the second object or tracker 14 relative to the second zone 38 from the second view 20*b*. Thus, the GUI 44 enables the user to readily see the actual location of the objects or trackers 12, 14 relative to the zones within the field of view 20.

The image representations of the zones and positions of objects or trackers 32, 38, 22, 24 mentioned above are shown to have similar shapes. For example, the first zone 32 is a circular outline and the position 22 of the first object or tracker 12 is a solid circle. In one example, this geometric selection is derived from a cross-section of the underlying geometry of the zone comprising a spherical ranges of acceptable positions as well as a simplification of the object or tracker as a point (circle) in space. However, the zones and objects or trackers may be represented in a manner that may be intuitive to the user, yet not derived from the underlying geometry of the object.

Hence, the image representations of the zones 32, 38 and positions 22, 24 of objects or trackers 12, 14 may be any suitable shape, size, and/or color. Additionally, corresponding zones and objects or trackers may be different shape, size, and/or color from each other. For example, the first zone 32 may be represented as a square outline and the position 22 of the first object or tracker 12 may be represented as a solid circle. As used herein, the term "outline" is generally defined as a perimeter or boundary line of the zone as displayed on the GUI 44.

The GUI 44 is configured to represent updates to the position 22 of the first object or tracker 12 relative to the first zone 32 and the position 24 of the second object or tracker 14 relative to the second zone 38. For example, if the position 22 of the first object or tracker 12 changed in space, the camera 16 detects the change in position and the GUI 44 is configured to produce real-time updates of the position 22 of the first object or tracker 12 relative to the first zone 32. This way, the user can immediately react to how changes in object or tracker position in space affect changes to the displayed object or tracker position relative to the displayed zone on the GUI 44.

In some examples, the represented object or tracker image (e.g., the circle or dot) 22, 24 can be manipulated in size to provide a 3D effect for the 2D views 20a, 20b. For example, the closeness or depth of the objects or trackers 12, 14 from the camera 16 may be represented on the GUI 44 by increasing or decreasing the 2D size of the represented object or tracker image 22, 24 in the "front view" as shown in FIG. 5. As the camera 16 moves closer to the objects or trackers 12, 14, the represented images 22, 24 may increase in size proportional to the distance of the camera 16 from the objects or trackers 12, 14. Similarly, the represented images 22, 24 may decrease in size as the camera 16 moves further away from the objects or trackers 12, 14. Although the dimension of depth is captured by the "top view", this technique provides the user with additional perspective about the depth for the "front view".

Similarly, the height of the objects or trackers 12, 14 relative to the camera 16 may be represented on the GUI 44 by increasing or decreasing the 2D size of the represented object or tracker image 22, 24 in the "top view" as shown in FIG. 5. As the camera 16 moves to a position above the position of the objects or trackers 12, 14, the represented images 22, 24 may decrease in size proportional to the distance of the camera 16 relative to the objects or trackers 12, 14. Similarly, the represented images 22, 24 may increase in size as the camera 16 is lowered towards the height of the objects or trackers 12, 14. Although the dimension of height is captured by the "front view", this technique provides the user with additional perspective about the depth in the "top view".

Referring back to FIG. 4, and at step 216, an evaluation is made about whether the objects or trackers 12, 14 are within the respective zones on the GUI 44. Step 216 may be performed manually by the user and/or automatically by the controller 18 and GUI 44. Manually, the user may visually inspect the GUI 44 to see whether the position 22 of the first object or tracker 12 is within the first zone 32 and/or whether position 24 of the second object or tracker 14 is within the second zone 38.

In another configuration, the GUI 44 is configured to produce feedback in response to the controller 18 automatically evaluating the position 22 of the first object or tracker 12 relative to the first zone 32 and the position 24 of the second object or tracker 14 relative to the second zone 38. More specifically, the controller 18 evaluates whether the objects or trackers 12, 14 are within or outside of the respective zones on the GUI 44.

As used herein, the term "within" is generally defined as the entirety of the image representation of the position 22 of the first object or tracker 12 or the position 24 of the second object or tracker 14 is within or inside the boundary lines of the zones, respectively. In one instance, if an edge of the image representation of the position 22 of the first object or tracker 12 is tangential along the boundary lines of the first zone 32 with the rest of the image representation of the position 22 of the first object or tracker 12 being within the boundary lines of the first zone 32, the position 22 of the first object or tracker 12 is considered within the first zone 32. As used herein, the term "outside" is generally defined as a portion of the image representation of the position 22, 24 of the first object or tracker 12 or second object or tracker 14 is not within the outline or boundary lines of the zones 32, 38, respectively. For example, as shown in FIG. 5, a portion of the image representation of the position 22 of the first object or tracker 12 from the top view 20b is not, in its entirety, within the boundary lines of the first zone 32. In this example, the position 22 of the first object or tracker 12 is considered to not be within or outside the first zone 32.

Again, any of the techniques or steps described above may be implemented and visualized using augmented reality, mixed reality, virtual reality, or any combination thereof.

The GUI 44 may produce a first feedback type 228 for an undesirable status for camera 16 positioning. More specifically, the GUI 44 may produce a first feedback type 228 in response to the controller 18 determining that the position 22 of the first object or tracker 12 is not within or outside of the first zone 32 or in response to the controller 18 determining the position 24 of the second object or tracker 14 is not within or outside of the second zone 38. If either the position 22 of the first object or tracker 12 or the position 24 of the second object or tracker 14 is not within the zones 32, 38, respectively, the method 200 transitions from step 216 to step 228 and the first feedback type 228 is produced. Examples of the first feedback type 228 are described below.

At step 228, the GUI 44 may also be configured to produce a recommendation 48 based on the controller 18 evaluating the position 22 of the first object or tracker 12 relative to the first zone 32 and/or the position 24 of the second object or tracker 14 relative to the second zone 38. The recommendation 48 may comprise information to aid in positioning of the camera 16 relative to the first and second objects or trackers 12, 14 based on the outcome of the evaluation. For example, as shown in FIG. 5, the recommendation 48 may be to reposition the camera 16 back 1 foot in response to the controller 18 determining that positions 22, 24 are partially beyond zones 32, 38, respectively (i.e., the camera 16 is too close to the objects or trackers 12, 14). In another example, the recommendation 48 may be to angle the camera 16 with respect to an angle difference between the normal direction of objects or trackers 12, 14 and the normal direction of the camera 16. The normal direction is a direction perpendicular to the primary operational surface of an object (e.g., perpendicular to a camera lens or to an emitter surface). Further, the angle difference may be displayed on the GUI 44 to aid in aligning the objects or trackers 12, 14 and the camera 16. The GUI 44 may immediately provide any number of recommendations 48 based on real-time controller 18 evaluations.

At step 230, the camera 16 may be required to be repositioned by the user. The repositioning of the camera may be performed manually by a user or performed using a semi-autonomous or fully-autonomous positioning system.

Once the camera 16 is repositioned, the method 200 can repeat steps 212-216 to recheck whether the repositioned camera 16 satisfies the system requirements for acceptable placement.

The user may interrupt or redefine the steps 202-230 of the method 200 at the user's discretion. The transition of any steps 202-230 of the method 200 may be interrupted by a user at any time. Interruptions may include, but not limited to, exiting the software, requesting a restart of the software, and the like.

On the other hand, the GUI 44 may produce a second feedback type 218 for a desirable status for camera 16 positioning. For example, the GUI 44 may produce the second feedback type 218 in response to the controller 18 determining that the position 22 of the first object or tracker 12 is within the first zone 32 or in response to the controller 18 determining the position 24 of the second object or tracker 14 is within the second zone 38. Alternatively, if both the position 22 of the first object or tracker 12 and the position 24 of the second object or tracker 14 are within the zones 32, 38, respectively, the second feedback 218 type is produced.

In one configuration, the first feedback 228 and second feedback 218 are different types of visual feedback. For example, the first feedback 228 may be a red indicator and the second feedback 218 may be a green indicator. These lights may be a perimeter or solid-fill coloring of the zone or the represented position of the object or tracker. Other types of visual feedback include arrows that may appear to guide the user to reposition the camera 16 in the direction of the arrows.

In another configuration, the first feedback 228 and the second feedback 218 may be audible. The first feedback 228 may be an alarm (a positive chime) and the second feedback 218 may be a different type of alarm (a negative chime). In another example, the alarm may gradually increase in frequency, tone, or tempo as the tracked position approaches the respective zone.

The feedbacks 228, 218 may be any combination of any suitable indicator disposed at any suitable location. For example, feedback 228 may be a red blinking light disposed on the display device 118 and feedback 218 may be an alarm disposed on the camera 16.

The GUI 44 may be configured to produce a plurality of different type of feedbacks such as haptic, tactile, force, or the like.

According to one example, if the camera position is satisfactory after step 216, the method 200 may skip to step 226 wherein the user may determine or decide that the camera 16 position relative to the objects or trackers 12, 14 is acceptable for the surgical procedure, thereby ending the procedure.

However, in some instances, an additional layer of evaluation may be needed for camera 16 positioning. In particular, method 200 provides for evaluation of the camera 16 position in view of a range of motion of the objects or trackers 12, 14 that is anticipated during the procedure. This way, the camera 16 position will be suitable for even the "worst-case" scenario movement of the objects or trackers 12, 14.

Accordingly, at step 220, the GUI 44 may be configured to request manual movement of the first and second objects or trackers 12, 14 throughout a range of motion. Step 220 may be executed by the user with or without the request from the GUI 44.

FIGS. 6A and 6B illustrate an example of how actual range of motion of the objects or trackers 12, 14 affects the display thereof on the GUI 44, and hence camera 16 positioning.

In FIG. 6A, the first object or tracker 12 is attached to the femur bone of the patient's leg and the second object or tracker 14 is attached to the tibia bone of the patient's leg with the leg in a flexion position. The flexion position of the leg represents on end of the range of motion of the objects or trackers 12, 14. The GUI 44 is shown producing the front view 20a of the field of view 20 relative to the camera 16 and the top view 20b of the field of view 20 relative to the camera 16. In the flexion position, the positions 22, 24 of the first object or tracker 12 and second object or tracker 14 are within the first and second zones 32, 38, respectively. Hence, the user or controller 18 can confirm that the camera 16 is suitably positioned at least for this end of the range of motion (at step 222).

The patient's leg (along with the first and second objects or trackers 12, 14) is also moved to an extension position (or vice-versa) shown in FIG. 6B. The extension position of the leg represents the opposing end of the range of motion of the objects or trackers 12, 14. The GUI 44 updates the positions 22, 24 of the first and second object or trackers 12, 14 throughout the range of motion. The dotted lines are provided for comparative purposes to show movement of the positions 22, 24 of the first and second objects or trackers 12, 14 between the flexion and extension positions of the leg. In the extension position, the positions 22, 24 of the first object or tracker 12 and second object or tracker 14 remain within the first and second zones 32, 38, respectively. Hence, the user or controller 18 can confirm that the camera 16 is suitably positioned for this other end of the range of motion (at step 222).

If the outcome of step 222 is successful (i.e., the objects or trackers 12, 14 fall within the zones throughout the range of motion), then the GUI 44, at step 224, can provide positive feedback according to any of the techniques described herein, or equivalents thereof. The user or controller 18 can accept the current placement of the camera 16 at step 226 and the positioning procedure for the camera 16 can terminate. The positioning procedure can be automatically reset in response to the controller 18 detecting change of the camera 16 position from the set location according to the procedure.

On the other hand, it is possible that the position 22 of the first object or tracker 12 is not within the first zone 32 or the position 24 of the second object or tracker 14 is not within the second zone 38, at any time throughout the range of motion. In such instances, the outcome of step 222 is not successful. The GUI 44, at step 228, can produce negative feedback indicating that the camera 16 is not in an acceptable position, as described. Repositioning of the camera 16 can recommence, as described at step 230. The process can continue until the camera 16 eventually is positioned in an acceptable manner.

In one configuration, where the range of motion of the patient's leg is predefined during the pre-operative planning, the first and second zones 32, 38 may be adjustable based on the position of the patient's leg or the robotic manipulator 102. For example, the first or second zones 32, 38 may move as the patient's leg is moved from extension to flexion or vice-versa. The GUI 44 may update the first or second zones 32, 38 as the objects or trackers 12, 14 are moved through the range of motion. Additionally, the position of the patient's leg in extension and the position of the patient's leg in flexion may be saved to the memory 50 of the computer 116. Based on the saved position of the patient's leg in extension and flexion, the controller 18 may automatically determine that the first and second objects or trackers 12, 14 are within the zones 32, 38 (step 222). Then the controller 18 may automatically advance to accepting the camera 16 positioning (step 226) and proceeding with the surgical procedure.

III. Range Finder

The system 10 may optionally include one or more range finders 29, as shown in FIG. 1.

The range finder 29 is configured to provide a primary or supplemental aid in positioning of the camera 16. In one example, the range finder 29 supplements any of the techniques above by providing a coarse positioning of the camera 16 relative to the objects or trackers 12, 14 and the GUI 44 may be utilized for more fine-tuning of camera 16 positioning. Alternatively, the range finder 29 can be utilized instead of the other methods described herein. The range finder 29 may provide accurate relative distance between camera 16 and anatomy, absent any tracker presence or detection, for aiding in camera 16 positioning.

The range finder 29 may also help in positioning of the camera 16 relative to any other target objects (tracked or not) in the operating room. For example, the camera 16 may be positioned relative to a surgical table before the attachment of the trackers 12, 14. In another example, the camera 16 may be positioned relative to the robotic manipulator 102.

As shown in FIG. 1, the range finder 29 is coupled to the camera 16. In one example, the range finder 29 may be integrally formed to the camera 16. In another example, the range finder 29 may be removably coupled to the camera 16. In yet another example, the system 10 may comprise two cameras 16 and the range finder 29 may be disposed between the cameras 16. The range finder 29 may couple to the camera 16 by any suitable method including, but not limited to, adhesives, fasteners, mounts and the like. Alternatively, the range finder 29 may be located at any suitable location for the system 10.

In another example, the camera 16, the controller 18, and the range finder 29 may be integrated into a single unit comprising an internal power supply such that the range finder 29 may be utilized without the requirement of powering up the entire system 10.

The range finder 29 may be configured to communicate with the camera 16 and/or the controller 18. The components of the range finder 29 may be connected to the camera 16 and/or the controller 18 by any form or medium of digital data communication mentioned above.

The controller 18 may be configured to define parameters, such as an acceptable distance range, an acceptable distance, and/or an acceptable orientation of the camera 16 relative to the objects or trackers 12, 14 or any other objects in the operating room. Alternatively, the user may set these parameters. The parameters may be adjustable by the controller 18 and/or the user depending on the type of surgical procedure. Accurate orientation and distance placement of the camera 16 ensures visibility of the objects or trackers 12, 14 throughout the surgical procedure and optimal localization accuracy.

The acceptable distance may be, for example, the distance between the camera 16 and the patient, e.g., 4 feet. The acceptable distance range, in this example, may be from 3.75 feet to 4.25 feet. In other words, the acceptable distance range is set to be +/−0.25 feet from the acceptable distance of the camera 16.

The acceptable orientation may include the direction of the camera 16 and the height of the camera 16 relative to the objects or trackers 12, 14 and/or any other object in the operating room. For example, the camera 16 may be positioned 7 feet from the floor and directed towards the surgical site such that the field of view 20 encompasses any desired objects. The direction may be defined as range of degrees (angle) measured by the position of the camera 16 as the origin wherein the object should fall within the range of degrees. This degree range may be 5, 15, or 20 degrees, for example.

The acceptable distance, distance range, and orientation may be predefined before the set-up of the camera 16 and/or the range finder 29 in the operating room. For example, calibration data or optimal performance characteristics for the range finder 29, camera 16, or objects or trackers 12, 14 may be stored in memory for defining the acceptable distance, distance range, and orientation.

Alternatively, the acceptable distance, distance range, and orientation may be dynamically defined during the set-up of the camera 16 and/or the range finder 29 in the operating room.

Once the acceptable distance, distance range, and orientation are defined, the range finder 29 aids in coarse positioning of the camera 16 by providing actual distance, distance range and orientation of the camera 16.

The range finder 29 may use any one or more of the following technologies: laser, radar, sonar, ultrasonic, and/or LIDAR.

In one example, the range finder 29 is a laser ranger finder. The laser range finder 29 may comprise one or more transmitters 29a for transmitting a beam of light and receivers 29b for receiving the reflected laser beam. The transmitter 29a may be a laser pointer. The laser pointer 29a may be configured to emit or transmit a laser beam to a target or object. The object reflects the laser beam back to the receiver 29b. The receiver 29b may be any LED detector, photodetector and the like.

The laser range finder 29 may comprise any number of transmitters 29a configured to aid in coarse positioning of the camera 16. In one example, the laser range finder 29 may comprise one transmitter 29a. The transmitter 29a emits a laser beam configured to aid in orientation pointing of the camera 16. In another example, the laser range finder 29 may comprise two transmitters 29a wherein the laser beams are angled relative to one another such that the two laser beams, dots are coincident when the camera 16 is at the acceptable distance from the target object(s).

The laser range finder 29 may comprise a measurement device and a calculation device. The measurement device is configured to measure the time the light beam takes to be emitted from the transmitter 29a until the light beam is reflected back to the receiver 29b. Thereafter, the calculation device is configured to compute the distance, orientation, or position of the object and/or the camera 16 based on the time measurement.

In one configuration, the measurement device and the calculation device are integrated with the laser range finder 29. In another configuration, the measurement device and the calculation device are integrated as software modules in the controller 18. In yet another configuration, the measurement device and the calculation device are in different locations. For example, the measurement device may be coupled to the laser range finder 29 and the calculation device may be coupled to the controller 18.

The range finder 29 is now described as a supplemental feature with respect to the system 10 as described above. For simplicity, the description below refers to the first object or tracker 12 and the second object or tracker 14 of the system 10. Of course, the techniques may work with any other objects, as described.

The controller 18 may be configured to receive data regarding the actual distance, distance range, and orientation from the camera 16 and/or the laser range finder 29. An evaluation is made by the controller 18 about whether the camera 16 is within the acceptable distance, distance range and orientation relative to the objects or trackers 12, 14. Alternatively, the user may visually evaluate whether the camera 16 is within the acceptable distance range and orientation relative to the objects or trackers 12, 14.

The controller 18 generates the GUI 44 to provide feedback to the user relating to the laser range finder 29. More specifically, a feedback regarding the acceptable distance, distance range and orientation of the camera 16 relative to the objects or trackers 12, 14 for fine-tuning of the camera 16 positioning.

The GUI 44 may produce a feedback similar to the feedbacks 228, 218 described above. Additionally, the GUI 44 may produce a numeral display of the acceptable distance, distance range, and/or orientation and the actual distance, distance range, and/or orientation of the camera 16 relative to the objects or trackers 12, 14. For example, the numeral display may be the acceptable height and actual height of the camera 16 from the floor.

The GUI 44 may be configured to also produce a recommendation 48a, such as the recommendations 48 described above. The recommendation 48a is based on the controller 18 evaluating the distance and orientation of the camera 16 relative to the objects or trackers 12, 14. The recommendation 48a may also comprise information to aid in positioning of the camera 16 relative to the objects or trackers 12, 14 based on the outcome of the evaluation. For example, the recommendation 48a may be to increase the actual height of the camera 16 by 1 foot.

In another configuration, the laser range finder 29 may produce the feedback regarding the camera 16 positioning. For example, the laser range finder 29 may emit a color change of the laser beam. The laser beam may be red to indicate increasing or decreasing of the distance of the camera 16 from the objects or trackers 12, 14 and the laser beam may be green to indicate the camera 16 is within the acceptable distance range.

In yet another configuration, the feedback relating to the laser range finder 29 may be implemented by LEDs mounted on the camera 16. For example, the LED may be color changing wherein the LED may be a red color LED to indicate increasing the distance of the camera 16, a blue color LED to indicate decreasing the distance of the camera 16, and a green color LED to indicate the camera 16 is within the acceptable distance range.

The system, method, and software provide technical solutions to technical problems that have not been addressed by prior techniques. The techniques described herein provide a technical solution for aiding in the placement of the camera at the appropriate position relative to the objects or trackers in 3D space. The techniques described herein eliminate repeated trial and error for camera setup. By providing zones for each object or tracker within the field of view, and representing the objects or trackers and zones on the graphical user interface, optimal positioning of the camera is readily possible. With the graphical user interface, the techniques can provide immediate feedback about whether the camera is placed too far/close, too high/low, or too far left/right relative to any one or more objects trackers. By showing several zones at once, the techniques account for proper positioning of the camera relative to several objects or trackers at once. Thus, the system, method, and software provide a technical solution to optimally satisfy this delicate balance involved with camera placement. In turn, the overall time required for preoperative setup is substantially decreased. Moreover, any detrimental consequences on the procedure resulting are mitigated because the techniques ensure proper positioning of the camera relative to static position of the objects or trackers as well as anticipated range of motion of the objects or trackers during a procedure. Accordingly, the techniques herein technologically provide a solution to determination of acceptable positioning for the camera, thereby increasing probability of a successful surgical procedure and eliminating repositioning of the camera during the surgical procedure. The system, method, and software may provide technical solutions other than those described above.

It will be further appreciated that the terms "include," "includes," and "including" have the same meaning as the terms "comprise," "comprises," and "comprising."

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A system comprising:
a display device;
a camera having a three-dimensional field of view and being configured to sense a position of a first surgical tracker and a position of a second surgical tracker in the field of view; and
a controller coupled to the camera and configured to:
define a first zone within the field of view, the first zone being positioned at a first location that is static relative to the field of view such that the first zone is located independent of the sensed position of the first surgical tracker, and the first zone defining a range of acceptable positions for the first surgical tracker relative to a position of the camera;
define a second zone within the field of view, the second zone being positioned at a second location that is different from the first location, the second location is static relative to the field of view such that the second zone is located independent of the sensed position of the second surgical tracker, and the second zone defining a range of acceptable positions for the second surgical tracker relative to the position of the camera;
receive the position of the first surgical tracker and the position of the second surgical tracker; and
execute a graphical user interface configured to aid in positioning of the camera to a location in an operating room relative to the first and second surgical trackers and the graphical user interface being configured to display simultaneously, on the display device, image representations of:
the field of view;
the first zone within the field of view at the first location;
the second zone within the field of view at the second location;
the position of the first surgical tracker relative to the first zone; and
the position of the second surgical tracker relative to the second zone.

2. The system of claim 1, wherein the first and second surgical trackers are each coupled to an anatomical part or a surgical instrument, and the controller is configured to receive the position of the first surgical tracker and the position of the second surgical tracker from the camera.

3. The system of claim 1, further comprising a laser range finder and wherein the controller is configured to receive the position of the first surgical tracker and the position of the second surgical tracker from the laser range finder.

4. The system of claim 1, further comprising a machine vision system and wherein the controller is configured to receive the position of the first surgical tracker and the position of the second surgical tracker from the machine vision system.

5. The system of claim 1, wherein the controller further defines each range of acceptable positions as a three-dimensional range of acceptable positions.

6. The system of claim 1, wherein the graphical user interface is further configured to display image representations of each of the field of view, the first and second zones, and the positions of the first and second surgical tracker in two-dimensional form.

7. The system of claim 6, wherein the graphical user interface is further configured to display image representations of the field of view with a first view and a second view, wherein the first view is a point-of view relative to the camera and the second view is a top view of the camera.

8. The system of claim 6, wherein the graphical user interface is further configured to display image representations of:
the position of the first surgical tracker relative to the first zone from a first view;
the position of the first surgical tracker relative to the first zone from a second view;
the position of the second surgical tracker relative to the second zone from the first view; and
the position of the second surgical tracker relative to the second zone from the second view.

9. The system of claim 1, wherein the graphical user interface is further configured to display actual image representations of the first and second surgical trackers combined with virtual image representations of the field of view and the first and second zones.

10. The system of claim 1, wherein the controller is configured to evaluate the position of the first surgical tracker relative to the first zone and the position of the second surgical tracker relative to the second zone.

11. The system of claim 10, wherein the graphical user interface is configured to display a recommendation in response to the controller evaluating of the position of the first surgical tracker relative to the first zone and the position of the second surgical tracker relative to the second zone, wherein the recommendation comprises information to aid in positioning of the camera to the location in the operating room relative to the first surgical tracker and the second surgical tracker.

12. The system of claim 10, wherein, in response to the controller evaluating the position of the first surgical tracker relative to the first zone and the position of the second surgical tracker relative to the second zone, the graphical user interface is configured to display:
a first feedback in response to the controller determining that the position of the first surgical tracker is outside of the first zone or in response to the controller determining that the position of the second surgical tracker is outside of the second zone; and
a second feedback that is different from the first feedback in response to the controller determining that the position of the first surgical tracker is within the first zone or in response to the controller determining that the position of the second surgical tracker is within the second zone.

13. The system of claim 1, wherein the controller is further configured to:
instruct the graphical user interface to request manual movement of the first and second surgical trackers through a range of motion; and
evaluate the position of the first surgical tracker relative to the first zone and the position of the second surgical tracker relative to the second zone during movement of the surgical trackers throughout the range of motion.

14. A method of operating a system comprising a camera having a three-dimensional field of view and being configured to sense a position of a first surgical tracker and a position of a second surgical tracker in the field of view, a display device, and a controller coupled to the camera, the method comprising:
defining, with the controller, a first zone within the field of view, the first zone being positioned at a first location that is static relative to the field of view such that the first zone is located independent of the sensed position of the first surgical tracker, and the first zone defining a range of acceptable positions for the first surgical tracker relative to a position of the camera;
defining, with the controller, a second zone within the field of view, the second zone being positioned at a second location that is different from the first location, the second location is static relative to the field of view such that the second zone is located independent of the sensed position of the surgical tracker, and the second zone defining a range of acceptable positions for the second surgical tracker relative to the position of the camera; receiving, with the controller, the position of the first surgical tracker and the position of the second surgical tracker; and
executing, with the controller, a graphical user interface to aid in positioning of the camera to a location in an operating room relative to the first and second surgical trackers and the graphical user interface displaying, simultaneously on the display device, image representations of:
the field of view;
the first zone within the field of view at the first location;
the second zone within the field of view at the second location;
the position of the first surgical tracker relative to the first zone; and
the position of the second surgical tracker relative to the second zone.

15. The method of claim 14, wherein the first and second surgical trackers are each coupled to an anatomical part or a surgical instrument, and further comprising the controller receiving the position of the first surgical tracker and the position of the second surgical tracker object from the camera.

16. The method of claim 14, further comprising a laser range finder and further comprising the controller receiving the position of the first surgical tracker and the position of the second surgical tracker from the laser range finder.

17. The method of claim 14, further comprising a machine vision system and further comprising the controller receiving the position of the first surgical tracker and the position of the second surgical tracker from the machine vision system.

18. The method of claim 14, further comprising the controller defining each range of acceptable positions as a three-dimensional range of acceptable positions.

19. The method of claim 14, further comprising the graphical user interface displaying image representations of each of the field of view, the first and second zones, and the positions of the first and second surgical trackers in two-dimensional form.

20. The method of claim 19, further comprising the graphical user interface displaying image representations of the field of view with a first view and a second view, wherein the first view is a point-of view relative to the camera and the second view is a top view of the camera.

21. The method of claim 19, further comprising the graphical user interface displaying image representations of:
- the position of the first surgical tracker relative to the first zone from a first view;
- the position of the first surgical tracker relative to the first zone from a second view;
- the position of the second surgical tracker relative to the second zone from the first view; and
- the position of the second surgical tracker relative to the second zone from the second view.

22. The method of claim 14, further comprising the graphical user interface displaying actual image representations of the first and second surgical trackers combined with virtual image representations of the field of view and the first and second zones.

23. The method of claim 14, further comprising the controller evaluating the position of the first surgical tracker relative to the first zone and the position of the second surgical tracker relative to the second zone.

24. The method of claim 23, further comprising the graphical user interface displaying a recommendation in response to the controller evaluating of the position of the first surgical tracker relative to the first zone and the position of the second surgical tracker relative to the second zone, wherein the recommendation comprises information to aid in positioning of the camera to the location in operating room relative to the first surgical tracker and the second surgical tracker.

25. The method of claim 23, wherein, in response to the controller evaluating the position of the first surgical tracker relative to the first zone and the position of the second surgical tracker relative to the second zone, further comprising the graphical user interface displaying:
- a first feedback in response to the controller determining that the position of the first surgical tracker is outside of the first zone or in response to the controller determining that the position of the second surgical tracker is outside of the second zone; and
- a second feedback that is different from the first feedback in response to the controller determining that the position of the first surgical tracker is within the first zone or in response to the controller determining that the position of the second surgical tracker is within the second zone.

26. The method of claim 14, further comprising the controller:
- instructing the graphical user interface to request manual movement of the first and second surgical trackers through a range of motion; and
- evaluating the position of the first surgical tracker relative to the first zone and the position of the second surgical tracker relative to the second zone during movement of the surgical trackers throughout the range of motion.

27. A non-transitory computer readable medium comprising instructions, which executed by one or more processors, implement a graphical user interface to aid in positioning of a camera to a location in an operating room relative to a first surgical tracker and a second surgical tracker, the camera having a three-dimensional field of view and being configured to sense a position of a first surgical tracker and a position of a second surgical tracker in the field of view, and a controller comprising the one or more processors and being coupled to the camera and configured to execute the graphical user interface to display, simultaneously on a display device, image representations of:
- the field of view of the camera;
- a first zone within the field of view, the first zone being positioned at a first location that is static relative to the field of view such that the first zone is located independent of the sensed position of the first surgical tracker, and the first zone defining a range of acceptable positions for the first surgical tracker relative to a position of the camera;
- a second zone within the field of view, the second zone being positioned at a second location that is different from the first location, the second location is static relative to the field of view such that the second zone is located independent of the sensed position of the second surgical tracker, and the second zone defining a range of acceptable positions for the second surgical tracker relative to the position of the camera;
- the position of the first surgical tracker relative to the first zone; and
- the position of the second surgical tracker relative to the second zone.

* * * * *